United States Patent [19]

Berenbaum et al.

[11] Patent Number: 5,220,087
[45] Date of Patent: Jun. 15, 1993

[54] PREPARATION OF STRONG AND SUPER ACID CATALYSTS USING ELEMENTAL FLUORINE

[75] Inventors: Morris B. Berenbaum, Summit; Thomas P. J. Izod, Basking Ridge; Donald R. Taylor, Randolph; John D. Hewes, Morristown, all of N.J.

[73] Assignee: Allied-Signal Inc., Morris Township, Morris County, N.J.

[21] Appl. No.: 806,483

[22] Filed: Dec. 13, 1991

[51] Int. Cl.⁵ .................. C07C 2/68; C07C 2/70; C07C 2/60
[52] U.S. Cl. .................. 585/462; 502/159; 521/31; 585/730; 525/356; 525/357
[58] Field of Search .............. 502/159; 585/730, 462; 521/31; 525/356, 357

[56] References Cited

U.S. PATENT DOCUMENTS

| | | | |
|---|---|---|---|
| 4,020,223 | 4/1977 | Dixon et al. | 428/224 |
| 4,076,916 | 2/1978 | Lagow | 526/43 |
| 4,264,750 | 4/1981 | Anand et al. | 525/356 |
| 4,296,151 | 10/1981 | Boultinghouse | 427/255.1 |
| 4,491,653 | 1/1985 | McGinniss et al. | 525/356 |
| 4,522,952 | 6/1985 | Klein et al. | 521/31 |
| 4,536,266 | 8/1985 | Bliefert et al. | 204/159.18 |
| 4,593,050 | 6/1986 | Cohen et al. | 522/2 |
| 4,828,585 | 5/1989 | Chiao | 55/16 |

FOREIGN PATENT DOCUMENTS 302345 6/1982 Fed. Rep. of Germany.
1453455 8/1965 France.

OTHER PUBLICATIONS

H. Brown, Dissertation, Technical Univ., Braunsweig, Germany, 1985.
J. U. Schlüter, Dissertation, Technical Univ. Braunsweig, Germany, 1987.

Primary Examiner—Asok Pal
Attorney, Agent, or Firm—Harold N. Wells; Mary Jo Boldingh; Gerhard H. Fuchs

[57] ABSTRACT

A fluorinated cation exchange resin catalyst is prepared by contacting a polymer containing pendant acid groups, particularly the radical —SO₃X with elemental fluorine in the presence of a water-free halogenated hydrocarbon liquid and thereafter converting the resulting pendant —SO₃X radical to a free acid.

14 Claims, 1 Drawing Sheet

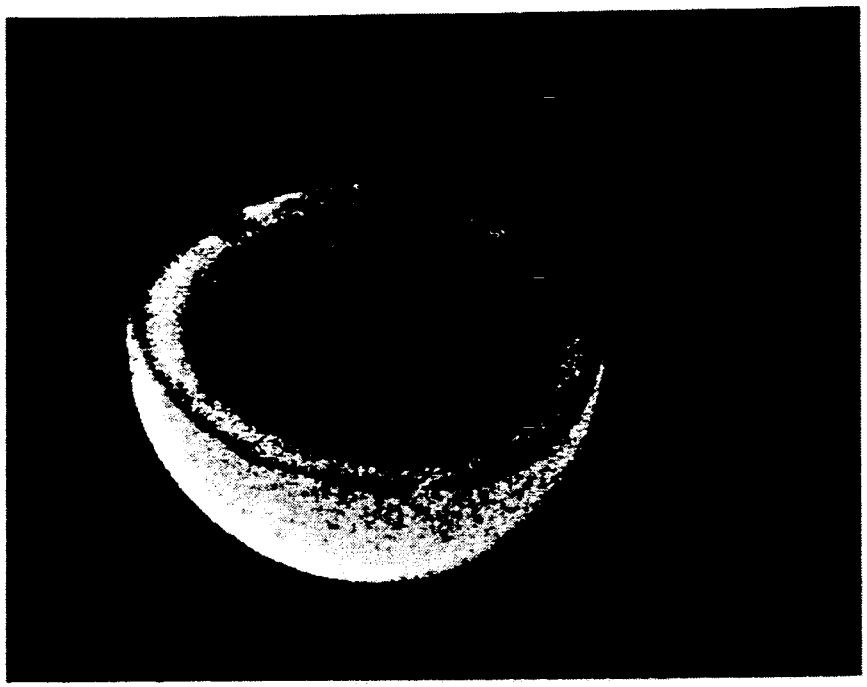
Figure 1 : $^{19}$F LMI – SIMS Cross-section of resin bead treated by liquid-phase fluorination process.
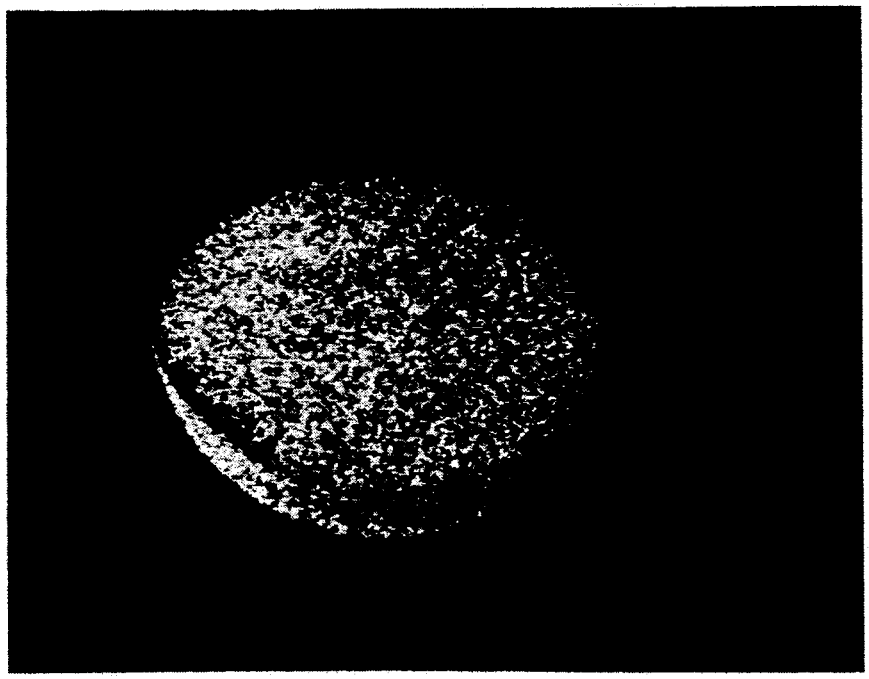
Figure 2 : $^{19}$F LMI – SIMS Cross-section of resin bead treated by gas-phase fluorination process.

PREPARATION OF STRONG AND SUPER ACID CATALYSTS USING ELEMENTAL FLUORINE

BACKGROUND OF THE INVENTION

The invention relates to strong and/or super acid catalysts, which have many potential uses. In particular, the invention relates to preparation of such catalysts by fluorinating polymers which contain pendant acid groups, such as sulfonic acid groups or their alkali metal salts.

Acid catalysts are employed in many commercial applications, such as oil refining and chemical processes, where acid catalysts such as $BF_3$, HF, $AlBr_3$, HBr, $AlCl_3$, HCl, $H_2SO_4$, $H_3PO_4$, zeolites, and ion exchange resins are found. In recent years, disposal of acids and hazards associated with their use have drawn the attention of the public and government regulators and consequently, there is an incentive to limit their use. To do so will require that substitutes be found which are efficient and which create fewer environmental problems.

One potentially useful material is acidic ion exchange resins, which are already employed in alkylation of aromatics and production of MTBE (methyl tertiary butyl ether). Typical of such resins are sulfonated macro reticular polystyrene/divinyl benzene resins such as Amberlyst 15 (Rohm and Haas), Dowex M-32 (Dow Chemical) and Lewatit (Bayer AG).

It is necessary to define the strength of acids in terms other than the familiar pH scale when one is discussing catalysts which may be characterized as strong or superacid catalysts. For purposes of the present invention the Hammett acidity scale will be used (1) Umansky, B., J. Engelhardt, W.K. Hall. *J. Catal.*, 1991, 127, 128–140; (2) Buttersack, C., H. Widdecke, J. Klein. *J. Mol. Catal.*, 1986, 35, 77–99.) Acids on this scale have a value from 0 to $-28$. When the value is below $-12$ (the strength of 100% $H_2SO_4$), the acid will be considered a superacid. For comparison, Amberlyst 15 has a Hammett acidity of $-2$, Nafion NR50 has a value of $-6.5$ to $-11$, 100% HF a value of $-11$, $BF_3/HF$ $-15$ and $HF/SbF_3$ $-28$ (Olah, G.A., G.K.S. Prakash, J. Sommer. "Superacids." New York: J. Wiley, 1985).

Fluorination of polymers has been suggested for various purposes. Dixon et al. in U.S. Pat. No. 4,020,223 disclose treatment of polyolefin and polyacrylonitrile fibers with fluorine in the presence of small amounts of oxygen to increase the amount of fluorination.

Fluorination of various polymers in the absence of oxygen but using a cold plasma was disclosed by Anand et al. in U.S. Pat. No. 4,264,750.

Functionalized polymers containing pendant ester, carboxylic acid, acid halide, or acid anhydride groups were fluorinated by fluorine-inert gas mixtures by Lagow as shown in U.S. Pat. No. 4,076,916.

Boultinghouse, in U.S. Pat. No. 4,296,151 discloses the fluorination of plastic articles with fluorine in an inert gas to make the surfaces more wettable with water. The polymers were based on hydrocarbons such as olefins, dienes, and vinyl-substituted aromatics.

McGinniss et al. in U.S. Pat. No. 4,491,653 examined the surface-fluorination of polymers and determined that the oxygen content should be restricted and that partial fluorination of the surface to produce —CHF— groups was desirable.

Chiao in U.S. Pat. No. 4,828,585 described the fluorination of gas separation membranes using fluorine and sulfur dioxide gases.

In U.S. 4,593,050 Cohen et al. disclose the use of ultraviolet light to assist in the fluorination of polymer surfaces using various fluorinated species, including fluorinated hydrocarbons.

Bliefert, et al. in U.S. 4,536,266 disclosed surface fluorination of various macromolecular materials by using elemental fluorine dissolved in liquids including halogenated hydrocarbons where the fluorine concentration is only $0.5 \times 10^{-3}$ to $1 \times 10^{-2}$ mol/l.

In U.S. Pat. No. 4,522,952 and DE 302345 SC2 Klein et al. disclosed a process for the fluorination of polymers and in particular those which contain sulfonic acid groups, $-SO_3H$, particularly $-SO_2F$, such as sulfonated crosslinked styrene/divinylbenzene. Klein et al. state that the group $-SO_3Na$ is undesirable since it produces products which tend to decompose. The fluorination reaction is carried out with the fluorine in the gas phase, beginning with a low concentration and gradually increasing until pure fluorine gas is used. The process is carried out at below ambient to ambient temperatures and without solvents. Klein et al. state their preference for replacing at least 90% of the hydrogen atoms in the polymer with fluorine atoms. The fluorinated polymer is said to have high catalytic activity for the alkylation of phenol with isobutane or benzene with propene.

In H. Brown, Dissertation, Technical Univ., Braunsweig, Germany, 1985; J. U. Schlüter, Dissertation, Technical Univ., Braunsweig, Germany, 1987, the fluorination of ion exchange resins was discussed. They reported that potassium- and cesium-exchanged resins were superior to those containing the acid group $-SO_3H$ and suggested adding alkali metal fluorides to increase the fluorination rate. The catalytic activity was found to reach a maximum at a degree of fluorination between 45 to 75%, with much reduced activity seen at either higher or lower levels of fluorination. The fluorination was carried out with fluorine in an inert gas and dilution of the fluorine was said to be important to avoid damage to the polymer matrix resulting in a loss of mechanical strength. The $-SO_3Na$ groups were found to be fluorinated with the lowest loss of $-SO_3H$ groups compared with fluorination of $-SO_2F$ and $-SO_2Cl$. Schlüter used fluorotrichloromethane (CFC-11) in conjunction with high flow rates of a fluorine/nitrogen gas mixture. The high gas flow rates used indicate that the reaction was primarily a gas-phase reaction by the uniform distribution of fluorine throughout the resin beads. Schlüter indicated that gas phase fluorination was preferred. This was also the conclusion in French patent 1,453,455 as reported by Klein et al.

The present inventors have sought and found an improved method for fluorinating porous polymers which is carried out in the presence of an inert diluent in the liquid phase and produces a highly active acid catalyst using less fluorine than the Klein et al. process and which avoids the mechanical degradation of the polymer resulting from a severe fluorination.

SUMMARY OF THE INVENTION

Improved fluorinated cation exchange resin catalysts are prepared by contacting with fluorine a macroporous polymer containing pendant acid groups, such as $-PO_3H_2$, $-COOH$, $-COH$, $-NO_2H$, $-COF$, and $-SO_3H$, particularly the radical $-SO_3H$, which is converted prior to fluorination to the acid salt radical —SO₃X where X is a cation from Group IA and IIA, such as Na, K, Cs, Ca, preferably Na. Elemental fluorine in an inert carrier gas is passed over the polymer in the presence of a water-free halogenated hydrocarbon liquid to form a fluorinated derivative. After fluorination, the acid salt radical —SO₃X is converted back to a free acid radical —SO₃H by hydrolysis and treatment with dilute aqueous acid. In one aspect, the invention includes stepwise wetting to avoid damage to the polymers and treating with HCl to convert the acid salt group to an acid group.

The fluorination is carried out at a temperature of about $-100°$ to $+20°$ C. at atmospheric pressure. The concentration of fluorine in an inert carrier gas (e.g nitrogen) is 0.5 to 60% based on volume. The contact time is a function of temperature and fluorine concentration.

In another aspect, the invention includes alkylation processes using the acid catalysts of the invention.

BRIEF DESCRIPTION OF THE FIGURES

FIG. 1 is a photo micrograph of a fluorinated polymer pellet of the invention.

FIG. 2 is a photo micrograph of a fluorinated polymer pellet of the prior art.

DETAILED DESCRIPTION OF THE INVENTION

The Catalyst

The catalyst of the invention may take various physical forms depending upon the particular applications, for example, as beds of solid particles or as a film or membrane. Other techniques for using the catalysts will suggest themselves to those skilled in the field of catalytic reactions.

Common to these applications is the presence as the catalytic agent of a polymer having acidic pendant groups which has been fluorinated at least partially to replace hydrogen atoms with fluorine atoms. Preferably, at least 2% and up to about 40% of the hydrogen atoms will be replaced by fluorine atoms. It is an advantage of the invention relative to that of Klein et al. described above that fewer of the hydrogen atoms are replaced, which not only reduces the cost of the catalyst but has been found to improve performance and minimizes the loss of mechanical strength of the polymer during the fluorination process. The process of fluorination used by the inventors is carried out in the presence of a liquid phase which permits improved control of the fluorination reaction. Also, the finishing steps used to wet the catalyst to the acid form avoid the physical damage to the polymer which can occur when a highly dried macroporous polymer is exposed to liquids.

The polymers which may be used in preparing catalysts of the invention may include those which contain pendant acidic groups such as —PO₃H₂, —COOH, —COH, —NO₂H, COF, and —SO₃H. In particular, the acidic group —SO₃H is preferred which may be converted to the —SO₃X group in the invention where X is a cation from Group IA or IIA, such as Na, K, Cs, or Ca. These groups may be attached directly to the polymer backbone or as in the Klein et al. patent through a pendant hydrocarbon group, such as an aromatic or aromatic alkyl group. It may be noted here that the sulfonated polystyrene/divinyl benzene which was of particular interest to Klein et al. is widely available as an ion exchange resin and, consequently, has advantages over other polymers. However, there are many other macroporous polymers which would suggest themselves to those skilled in the art and which could be converted to acidic catalysts by the methods of the present inventors. Examples of such polymers include polyacrylic acid and polyvinyl phosphoric acid.

In order for the catalyst to be effective, the polymer substrate should contain a relatively large number of pendant acidic groups, say at least about 8 to 20 of the carbon atoms in the polymer chain should be attached to an acid group. Preferably a larger number of pendant acid groups should be present and particularly up to about 2 to 12 atom % of the carbon atoms should have a pendant acid group. The pendant groups may be present as the polymer is produced or they may be added after the polymer is made. For example, when styrene and divinyl benzene are co-polymerized, the polymer has pendant aromatic groups, which are later sulfonated to produce the acidic ion exchange resin. Alternatively, a polymer such as sulfonated polystyrene/divinyl benzene may be produced by reacting vinyl sulfonic acid and divinyl benzene which thus already contains pendant acid groups as formed In another route a polymer may be made from 2-hydroxy ethyl-methacrylate and dimethacrylate and then acid groups attached to the surface by reaction with ClSO₃H. Whichever method is chosen, the polymer containing pendant acid groups is then fluorinated to produce the catalyst of the invention.

Making the Catalyst

While fluorination of polymer surfaces has been disclosed for various purposes, as has been previously described, and such methods could be employed to prepare a fluorinated polymer containing pendant acid groups, the present inventors have found a method which provides superior results and enables one to control the degree of fluorination and thereby to produce catalysts by virtue of the ability to control acid strength. Previous reports of fluorination in the presence of a liquid phase were not favorable and gas phase fluorination was recommended. However, the present inventors have found that when the polymer to be fluorinated is placed in a bath of a liquid solvent, particularly a fluorocarbon or chlorofluorocarbon, and then contacted with a stream of inert gas, such as nitrogen or helium, so that the polymer particles are suspended or fluidized by the upward flowing gas that fluorine gas can be introduced and reacted with polymer in a controlled fashion, producing a superior catalyst.

It has been found that gas phase fluorination produces inferior results, probably since (a) it is less able to remove the large amount of heat released during the fluorination process on a macroscopic scale, and (b) results in fluorination of internal pores of the ion exchange resin where catalysis might not occur, and thereby wasting fluorine gas. This gas phase fluorination is believed to result in less uniform and more destructive fluorination than can be achieved with the liquid phase fluidized bed reactor. In practice, the polymer particles will be suspended in the liquid by a stream of upflowing gas sufficient to prevent their settling in the reactor. This amount of gas will depend on the size and weight of the polymer particles but will generally require an upward superficial velocity of about $1 \times 10^{-5}$ to $1 \times 10^{-3}$ m/sec when the polymer particles have a diameter of between 0.1 and 0.5 mm. Obviously, the gas should be distributed uniformly across the containing vessels cross-section to provide as consistent results as possible and this may be done using methods familiar to those skilled in the art of reactor design.

The pendant acid groups will be converted to a form which minimizes fluorination of the acid groups. Where the acid groups are —$SO_3H$, they may be converted to the acid salt, i.e., the —$SO_3X$ form by reacting with compounds containing Group IA or IIA cations such as Na, K, Cs, Ca, sodium hydroxide, potassium hydroxide, cesium hydroxide, or calcium hydroxide.

The solvent to be used in the fluid bed reactor should be inert to the polymer and to gaseous fluorine. Thus, solvents which are water-free halogenated hydrocarbons are preferred, such as trichlorofluoromethane. Others may be used such as trichlorotrifluoroethane, perfluorohexane, and the like. These solvents should have an increased solubility of fluorine gas over other available solvents, have high wettability (low surface tension), and good thermal conductivity. The amount of the solvent will be selected based on the volume of the reactor in use and on the amount of polymer to be fluorinated. In general, the ratio of the solvent to the polymer would be about 12 vol.% to 3 wt.%.

Fluorine is added to an inert gas such as helium, nitrogen, argon, or sulfur hexafluoride in an amount which permits the fluorination to proceed in a controllable manner at flow rates which provide a superficial velocity of about $1 \times 10^{-5}$ m/sec to $1 \times 10^{-3}$ m/sec. In general the inert gas mixture will contain about 0.5 to 60% fluorine, which may be varied during the fluorination process The fluorination process will be carried out at temperatures in the range of about $-100°$ to $+20°$ C., preferably about $-50°$ to $-20°$ C. The pressure in the reactor will vary depending on the temperature, the concentration of fluorine in the inert gas, and the degree of fluorination desired. Typically, the process will be operated at atmospheric pressure. The time required for fluorination of the polymer will depend on the conditions of operation and the degree of fluorination desired, consequently, the process may take from about 5 min. to 15 days.

After completion of the fluorination step, the —$SO_3X$ group will be wetted and then converted to the acid form. It has been found that this step must be done very carefully to avoid physical damage to the fluorinated polymer. A typical procedure is given in Example 2 below, but it may generally be characterized as requiring washing with water, following by hydrolysis with NaOH and conversion with HCl. A critical step is the initial contacting of the polymer with water, which should be done slowly with finely atomized water particles, preferably of about 2 μm diameter or smaller. After this initial moistening, the polymer may be freely immersed in water.

Using the Catalyst

There are many processes in which the catalysts of the invention may be used, since they have strong or superacid properties. Thus, potentially such catalysts may be used to replace liquid and supported acid catalysts such as $BF_3$, HF, $AlBr_3$, HBr, $AlCl_3$, HCl, $H_2SO_4$, $H_3PO_4$, zeolites, and acidic ion exchange resins. Typical reactions where the catalysts may have application include isomerization, alkylation, polymerization, dehydration, etherification, and esterification.

One reaction of particular interest is the alkylation of aromatics with olefins, such as the alkylation of benzene with ethylene to produce styrene. Alkylation of aliphatics is also widely employed to produce high octane components for gasoline blending. In the examples below an alkylation reaction is employed to illustrate the application of the invention, but it should be understood that many other reactions may be carried out with catalysts of the invention.

EXAMPLE 1

Fluorination of Sulfonated Polystyrene

A jacketed 4 ft. × 1.5 in. diameter FEP (fluorinated ethylene polypropylene) (1.22 m × 38.1 mm i.d.) tube was used as a reactor and fitted with an exit port at the top and inlet port at the bottom. A sample of commercially available sulfonated polystyrene/divinyl benzene ion exchange resin beads having diameters of 0.1 to 0.5 mm was placed in the reactor and then it was filled with CFC-11. A mixture of fluorine in an nitrogen gas was introduced though a sparger at the bottom of the reactor at a predetermined rate and passed up through the polystyrene beads at a rate which caused them to be suspended in the liquid. The gas passed out the top of the reactor and was cooled to condense any volatile components and then scrubbed in $Al_2O_3$ and NaF traps to remove any remaining fluorine and any HF which was formed, respectively.

In one experiment the reactor was loaded with 50 g of 0.5 mm sulfonated polystyrene/divinyl benzene beads (M-32 Dow Chemical) which had the pendant acid groups converted to the —$SO_3Na$ form by contacting with 1N aqueous sodium hydroxide and then washed with water. The beads were washed with methanol and dichloromethane and dried to contain about 0.3 wt % water. Then, the reactor was filled with 1700 g of CFC-11 (trichlorofluoromethane) which had been dried over calcium sulfate to about 10 ppm water. A flow of 100 sccm ($6 \times 10^{-3}$ m$^3$/hr) of a gas mixture containing 25 vol.% fluorine and the remainder nitrogen was passed upwardly through the bed. Thus, the superficial velocity was about $3.2 \times 10^{-4}$ m/sec. The temperature was maintained at $-40°$ C. by passing cold methanol from a cryogenic bath through the jacket surrounding the reactor. After 80 hours the gas flow was cut off, the reactor purged with nitrogen to remove residual fluorine, and the reactor was warmed to ambient temperature. The fluorinated beads were then unloaded from the reactor. They were found to contain about 25.0 wt % fluorine by elemental analysis.

EXAMPLE 2

Wetting of the Fluorinated Polymer

The fluorinated polymer beads were dried under a flow of dry nitrogen and then contacted with water atomized to about 2 μm so that the beads moistened slowly. After 24 hours the wet polymer beads were submerged in water and left overnight. Then they were washed with water, hydrolyzed with 1N NaOH and converted to the acid form using 1N HCl. The beads were then dried for 72 hours under vacuum at 70° C. to a water content of less than 0.1 wt.% to complete the catalyst preparation.

EXAMPLE 3

Alkylation of Isobutane with Isobutylene

Into a jacketed glass reactor containing a preheat zone of glass beads and 13.6 mm internal diameter equipped with a 6 mm (O.D.) thermocouple well was placed, under a mild flow of pre-dried nitrogen, 9.88 grams of catalyst resin prepared as in Examples 1 and 2 and containing 19.71 wt.% fluorine, to a volume of 45 cm$^3$. The reactor bed was fitted to the gas inlet and outlet transfer lines and the heating jacket was attached to a thermostated bath, and the system was brought to a temperature of 100° C. using a flow of high purity nitrogen. Upon reaching 100° C., a feed of isobutane (30 mL/min), isobutylene (0.7 mL/min), and nitrogen (25 mL/min) was introduced (GHSV 72/hr). Product distributions were obtained from an online gas chromatograph equipped with an automated gas-sampling loop. Peak retention times obtained from the gas chromatograph were compared with known standards obtained from commercial sources. Data analysis indicated a produce distribution of 2.0% C$_5$, 4.8% C$_6$, 5.4% C$_7$, 87.9% C$_8$, and 0.2% greater than or equal to C$_9$ hydrocarbons.

EXAMPLE 4

Alkylation of Toluene with Propylene

Into a jacketed ⅜"×16" (9.5 mm×405 mm) stainless steel reactor containing a ⅛"×13" (3.2 mm×330 mm) thermocouple well and a crushed quartz pre-heat zone was placed 6.47 g (9.9 mL) of a catalyst prepared as in Examples 1 and 2 and containing 19.71 wt.% fluorine. The reactor temperature was raised to 55° C. with hydrogen purge, and then a feed stream consisting of pre-dried toluene and propene (5 wt.%, 10.4 mol % in nitrogen) was fed into the reactor at a pressure of 700 p.s.i.g. (4826 kPa gage) and LHSV of 4.5 hr$^{-1}$. The products consisted of 40% ortho-, 15% meta- and 45% para-methyl-iso-propyl-benzene obtained at a total conversion of 74 mol %, compared with a conversion of 55% obtained from a control catalyst in which the polymer had not been fluorinated.

EXAMPLE 5

Alkylation of Toluene with Ethylene

The same reactor used in Example 4 was charged with a feedstock containing a (3.6 wt.%, 10.4 mol %) concentration of ethylene in toluene. At a reaction temperature of 100° C., 5.95 g (9.0 mL) of a catalyst analyzed to contain 19.71 wt.% fluorine gave 49.4% ortho-, 22.7% meta-, and 27.9% para-ethyl-methyl-benzene with 44.4 mol % conversion, compared to 17.1 mol % conversion for a control catalyst in which the polymer had not been fluorinated.

EXAMPLE 6

Comparative

Samples of fluorinated polymer beads prepared as in Example 1 were fluorinated by F$_2$ in nitrogen but without the presence of the liquid phase used in Example 1. The concentration of F$_2$ in nitrogen was 2.5 vol% and the superficial velocity was 1.07×10$^{-4}$ m/sec. The gas phase fluorination was carried out for 40 hours at −60° C. and atmospheric pressure.

Analysis of the samples by x-ray photoelectron spectroscopy (XPS) and liquid metal ion-secondary ion mass spectrometry (LMI-SIMS) showed that the outer surface of the beads prepared according to the invention had a highly fluorinated surface extending inward to a depth of about 13% of the bead diameter. In contrast, the beads fluorinated in the gas phase appeared to be uniformly reacted throughout. This liquid phase surface fluorination method provides a greater ratio of —CF$_2$— to —CHF— groups and is believed to be an advantage in catalytic applications. Fluorination according to the invention, i.e., in the presence of a liquid, is compared to gas phase fluorination in FIGS. 1 and 2. FIG. 1 clearly shows the presence of a localized surface fluorination while FIG. 2 shows that with gas phase fluorination the effect of fluorine is distributed through the polymer bead.

We claim:

1. A process for preparing a fluorinated cation exchange catalyst comprising contacting a hydrocarbon polymer containing pendant acid groups with elemental fluorine in the presence of a water-free halogenated hydrocarbon liquid to form a fluorinated derivative by replacing at least a portion of the hydrogen atoms in said polymer with fluorine atoms wherein said pendant acid groups are converted to acid salt groups before fluorination and thereafter converting the acid salt groups to acid groups by treatment with dilute aqueous acid.

2. The process of claim 1 wherein 2 to 12% of the carbon atoms of said polymer have pendant acid groups.

3. The process of claim 1 wherein at least 2% and up to about 40% of the hydrogen atoms in said polymer are replaced with fluorine atoms.

4. The process of claim 1 wherein said pendant acid groups are selected from the group consisting of —PO$_3$H$_2$, —COOH, —COH, —NO$_2$H, —COF, and —SO$_3$H.

5. The process of claim 3 wherein said pendant acid group is —SO$_3$H and said acid group is converted to —SO$_3$X where X is a cation selected from Group IA or IIA.

6. The process of claim 5 wherein the radical SO$_3$X is SO$_3$Na.

7. The process of claim 3 wherein catalyst is in particulate form and the rate of gas flow is sufficient to fluidize said particles.

8. The process of claim 1 wherein said contacting occurs at a temperature of about −100° to +20° C. and at atmospheric pressure.

9. The process of claim 1 wherein the fluorine has a concentration of 0.5 to 60 vol.% in an inert carrier gas.

10. The process of claim 1 wherein said polymer is selected from the group consisting of sulfonated macroreticular polystyrene/divinyl benzene ion-exchange resins.

11. The process of claim 5 wherein said radical —SO$_3$X is hydrolyzed after said fluorination by the steps of
    (a) drying the fluorinated polymer in nitrogen;
    (b) moistening the dried polymer with water atomized to about 2 μm or smaller;
    (c) immersing the moistened polymer of (b) in water;
    (d) hydrolyzing the product of (c) with NaOH;
    (e) converting the hydrolyzed produce of (d) to the acid form by treating with HCl.

12. The fluorinated cation exchange catalyst produced by the process of claim 1.

13. A process for alkylation of toluene with ethylene comprising passing said toluene and ethylene at alkylation conditions over a fluorinated cation exchange catalyst prepared by contacting a hydrocarbon polymer containing pendant acid groups with elemental fluorine in the presence of a water-free halogenated hydrocarbon liquid to form a fluorinated derivative by replacing at least a portion of the hydrogen atoms in said polymer with fluorine atoms wherein said pendant acid groups are converted to acid salt groups before fluorination and thereafter converting the acid salt groups to acid groups by treatment with dilute aqueous acid.

14. A process for alkylation of isobutane with isobutylene comprising passing said isobutane and isobutylene at alkylation conditions over a fluorinated cation exchange catalyst prepared by contacting a hydrocarbon polymer containing pendant acid groups with elemental fluorine in the presence of a water-free halogenated hydrocarbon liquid to form a fluorinated derivative by replacing at least a portion of the hydrogen atoms in said polymer with fluorine atoms wherein said pendant acid groups are converted to acid salt groups before fluorination and thereafter converting the acid salt groups to acid groups by treatment with dilute aqueous acid.

* * * * *